(12) United States Patent
Gill et al.

(10) Patent No.: US 10,793,851 B2
(45) Date of Patent: Oct. 6, 2020

(54) MULTIPLEXED BINARY ASSEMBLY AND QUANTITATIVE TRACKING OF BACTERIAL POPULATIONS

(71) Applicant: THE REGENTS OF THE UNIVERSITY OF COLORADO, a body corporate, Denver, CO (US)

(72) Inventors: Ryan T. Gill, Denver, CO (US); Ramsey Zeitoun, Gaithersburg, MD (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 297 days.

(21) Appl. No.: 15/749,540

(22) PCT Filed: Aug. 4, 2016

(86) PCT No.: PCT/US2016/045633
§ 371 (c)(1),
(2) Date: Feb. 1, 2018

(87) PCT Pub. No.: WO2017/024173
PCT Pub. Date: Feb. 9, 2017

(65) Prior Publication Data
US 2018/0230459 A1    Aug. 16, 2018

Related U.S. Application Data

(60) Provisional application No. 62/201,107, filed on Aug. 4, 2015.

(51) Int. Cl.
C12P 19/34 (2006.01)
C12N 15/10 (2006.01)
(Continued)

(52) U.S. Cl.
CPC ......... *C12N 15/1065* (2013.01); *C12N 15/10* (2013.01); *C12N 15/11* (2013.01);
(Continued)

(58) Field of Classification Search
None
See application file for complete search history.

(56) References Cited

U.S. PATENT DOCUMENTS 4,683,202 A    7/1987  Mullis
4,965,188 A   10/1990  Mullis et al.
(Continued)

OTHER PUBLICATIONS

Warner et al., Nature Biotechnology 28(8), pp. 856-863 (2010). (Year: 2010).*
(Continued)

*Primary Examiner* — Kenneth R Horlick
(74) *Attorney, Agent, or Firm* — Polsinelli PC

(57) ABSTRACT

Compositions and methods for tracking combinations of mutations in populations by coupling DNA assembly and paired-end sequencing technology with high-throughput sequencing. This allows for an unlimited number of mutation sites in a population of microorganisms to be identified, and allows sites to be sequenced across several replicates. Unique identifiers (DNA barcodes) can be used to measure fitness data by sequencing of the barcodes multiplexed with the mutation sites with high-throughput short sequencing read technology, allowing selections to be rapidly performed on populations of known combinatorial genotypes.

23 Claims, 13 Drawing Sheets

(51) Int. Cl.
| | |
|---|---|
| *C12N 15/11* | (2006.01) |
| *C40B 40/06* | (2006.01) |
| *C40B 50/06* | (2006.01) |
| *C12Q 1/686* | (2018.01) |

(52) U.S. Cl.
CPC .............. *C12Q 1/686* (2013.01); *C40B 40/06* (2013.01); *C40B 50/06* (2013.01); *C12Q 2525/191* (2013.01); *C12Q 2531/113* (2013.01); *C12Q 2535/122* (2013.01)

(56) References Cited

U.S. PATENT DOCUMENTS

| 5,023,171 | A | 6/1991 | Ho et al. |
|---|---|---|---|
| 6,204,025 | B1 | 3/2001 | Liu |
| 8,268,564 | B2 * | 9/2012 | Roth .................... C12Q 1/6816 435/6.12 |
| 8,467,975 | B2 | 6/2013 | Ryan et al. |
| 8,546,136 | B2 | 10/2013 | Serber et al. |
| 2007/0141048 | A1 | 6/2007 | Oleksiewichz et al. |
| 2017/0009283 | A1 | 1/2017 | Gill et al. |

OTHER PUBLICATIONS

International Search Report issued by the U.S. Patent and Trademark Office for International Patent Application No. PCT/US2016/045633, dated Nov. 29, 2016, 3 pages.

Written Opinion issued by the U.S. Patent and Trademark Office for International Patent Application No. PCT/US2016/045633, dated Nov. 29, 2016, 6 pages.

Chamberlain et al., "Deletion screening of the Duchenne muscular dystrophy locus via multiplex DNA amplification," Oxford Journals, Nucleic Acids Research, 1988, vol. 16(23), pp. 11141-11156.

Eckert et al., "DNA Polymerase Fidelity and the Polymerase Chain Reaction," PCR Methods and Applications, Cold Spring Harbor Laboratory Press, 1991, vol, 1(1), p. 17-24.

Ellis et al., "DNA assembly for synthetic biology: from parts to pathways and beyond," Integrative Biology, 2011, vol. 3(2), pp. 109-118.

Griffiths et al., "Miniaturising the laboratory in emulsion droplets," Trends in Biotechnology, vol. 24, No. 9, Sep. 2006, pp. 395-402.

Hass, "Mutational Evidence for a Structural Model of the Lassa Virus RNA Polymerase Domain and Identification of Two Residues, Gly1394 and Asp1395, That are Critical for Transcription but not Replication of the Genome," Journal of Virology, vol. 82, No. 20, Oct. 2008, pp. 10207-10217.

Heckman et al., "Gene splicing and mutagenesis by PCR-driven overlap extension," Nature Protocols, 2007, vol. 2(4), pp. 924-932.

Innis, "PCR Protocols: A Guide to Methods and Applications-Optimization of PCRs," Academic Press, Inc., San Diego, CA, 1990, pp. 3-12, 11 pages.

Kapoor, "Sequencing Human Mitochondrial Hypervariable Region II as a Molecular Fingerprint for Environmental Waters," Environmental Science & Technology, vol. 48, No. 18, 2014, pp. 10648-10655.

Lievre et al., "KRAS Mutation Status is Predictive of Response to Cetuximab Therapy in Colorectal Cancer," Cancer Research, vol. 66, No. 8, Apr. 2006, pp. 3992-3995.

Mattila et al., "Fidelity of DNA synthesis by the Thermococcus litoralis DNA polymerase—an extremely heat stable enzyme with proofreading activity," Oxford University Press, Nucleic Acids Research, 1991, vol. 19(18), pp. 4967-4973.

Paez et al., "EGFR Mutations in Lung Cancer: Correlation with Clinical Response to Gefitinib Therapy," Science, vol. 34, Jun. 2004, pp. 1497-1500.

Porter et al., "Lentiviral and targeted cellular barcoding reveals ongoing clonal dynamics of cell lines in vitro and in vivo," Genome Biology, vol. 15, No. 5, pp. 1-14, (2014).

Saiki, et al. "Enzymatic Amplification of β-Globin Genomic Sequences and Restriction Site Analysis for Diagnosis of Sickle Cell Anemia," Science, 1985, vol. 230, pp. 1350-1352.

Sandoval et al., "Strategy for directing combinatorial genome engineering in *Escherichia coli*," PNAS Early Edition, 2012, retrieved from www.pnas.org/cgi/doi/10.1073/pnas.1206299109, 6 pages.

Schorpp et al., "The human ubiquitin C promoter directs high ubiquitous expression of transgenes in mice," Nucleic Acids Research, vol. 24, No. 9, 1996, pp. 1787-1788.

Wang et al., "Multiplexed Genome Engineering and Genotyping Methods: Applications for Synthetic Biology and Metabolic Engineering," Methods in Enzymology, Chapter Eighteen, 2011, vol. 498, pp. 409-426.

Wang et al., "Programming cells by multiplex genome engineering and accelerated evolution," Nature-Letters, 2009, vol. 460, 14 pages.

Wetmur et al., "Molecular haplotyping by linking emulsion PCR: analysis of paraoxonase 1 haplotypes and phenotypes," Oxford Journals, Nucleic Acids Research, 2005, vol. 33(8), pp. 2615-2619.

Williams et al., "Amplification of complex gene libraries by emulsion PCR," Nature Methods, 2006, vol. 3(7), pp. 545-550.

Williams, "BioTechniques-Synthetic Bio: Expanding PCR's Repertoire | PCR Feature," biotechniques.com, 2012, retrieved from biotechniques.com/news/Synthetic-Bio-Expanding-PCRs-Repertoire/biotechniques-331496.html, 3 pages.

Yarden et al., "The ERBB network: at last, cancer therapy meets systems biology," Nature Reviews Cancer, vol. 12, No. 8, Jul. 2012, pp. 553-563.

Zeitoun et al., "Multiplexed tracking of combinatorial genomic mutations in engineered cell populations," Nature Biotechnology, vol. 33, No. 6, Mar. 23, 2015, pp. 631-637.

International Search Report and Written Opinion for International (PCT) Patent Application No. PCT/US15/15058, dated Apr. 28, 2015, 8 pages.

International Preliminary Report on Patentability for International (PCT) Patent Application No. PCT/US15/15058, dated Aug. 18, 2016, 7 pages.

International Search Report and Written Opinion for International (PCT) Patent Application No. PCT/US2016/045633, dated Nov. 29, 2016, 6 pages.

International Preliminary Report on Patentability for International (PCT) Patent Application No. PCT/US2016/045633, dated Feb. 15, 2018, 8 pages.

Official Action for U.S. Appl. No. 15/116,300, dated Apr. 5, 2018, 10 pages.

* cited by examiner

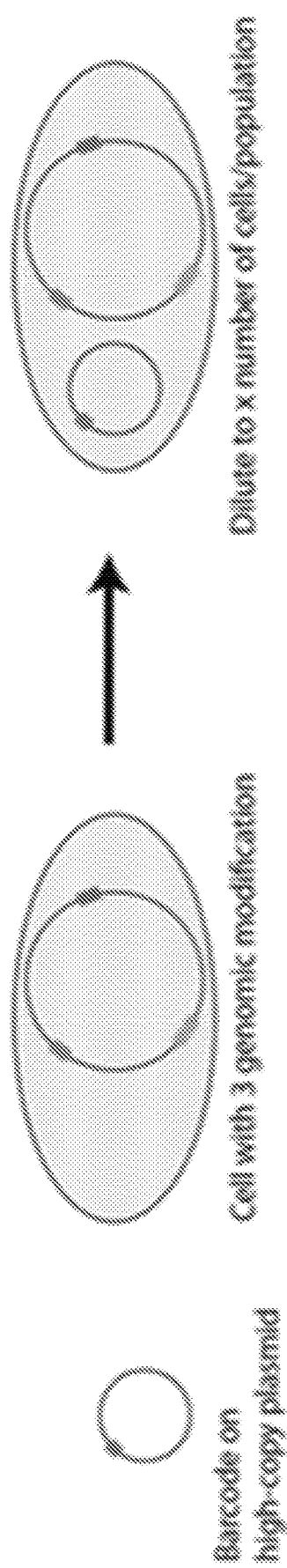
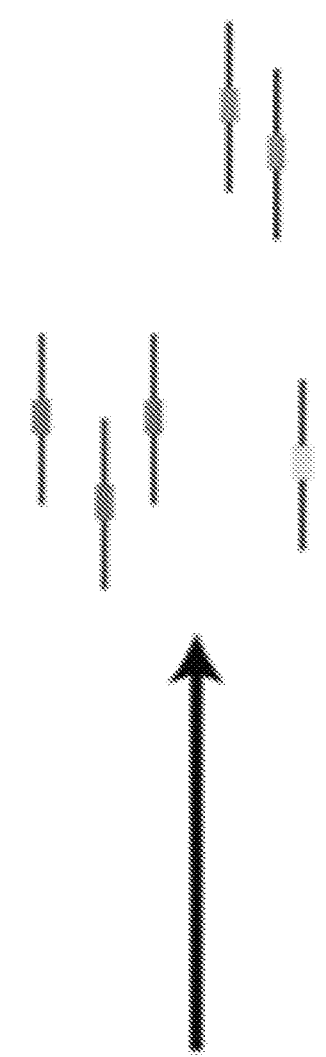
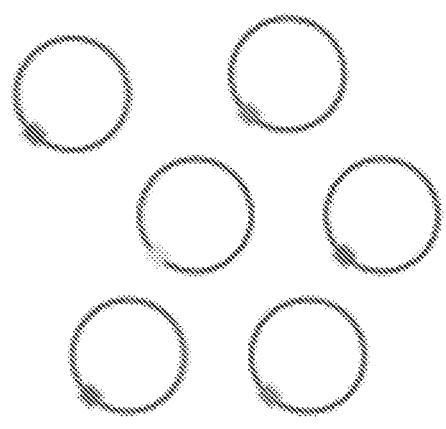
FIG. 1A
FIG. 1B

MULTIPLEXED BINARY ASSEMBLY AND QUANTITATIVE TRACKING OF BACTERIAL POPULATIONS

GOVERNMENT INTEREST

This invention was made with Government support under grant number DE-SC0008812 awarded by the U.S. Department of Energy, Office of Biological and Environmental Research, Genomic Science program. The U.S. Government has certain rights in this invention.

CROSS REFERENCE TO RELATED APPLICATIONS

This application is a national stage application under 35 U.S.C. 371 of PCT Application No. PCT/US2016/045633, having an international filing date of Aug. 4, 2016, claiming the benefit of priority to U.S. Provisional Patent Application Ser. No. 62/201,107 filed Aug. 4, 2015 These applications are incorporated herein by reference in their entirety for all purposes.

TECHNICAL FIELD

The invention relates generally to the field of synthetic biology and, more particularly, to improved methods for tracking combinations of mutations in cell populations by coupling DNA assembly with paired-end sequencing technology.

BACKGROUND

Assessing the effects of combinations of genetic mutations in heterogenous populations of cells (bacteria, eukaryotic etc.) has implications in metabolic and genetic engineering, disease diagnostics and synthetic biology. Particularly, individual genetic mutations conferring a phenotype when found alone, may result novel or unpredictable phenotypes in the presence of other mutations. But current genotyping methods do not adequately assess the effects of combinations of mutations found in heterogenous populations, and there are few high-resolution and high-throughput techniques for screening combinations of mutations that exist in a population.

Assembly of diverse genetic elements into a single vector traditionally required restriction and ligation enzyme-based methods that are time-consuming and laborious. For example, each sub-cloning step requires the resulting clone be screened and characterized before the introduction of additional fragments. Clones produced by blunt end ligation require confirmation that the fragment was introduced in the proper orientation, while sticky-end ligation requires that the restriction sites utilized to produce the sticky ends on the acceptor fragment also be present in the donor fragment, but not at a site that would interrupt the sequence of interest within the donor fragment. Thus, the selection of workable restriction sites depends entirely on the compositions of the pieces being joined and must be carefully considered in each case. Moreover, the efficiency of such restriction-enzyme based cloning methods is limited by the number of nucleic acid molecules that can be ligated together in a single reaction.

It has been shown that simultaneous amplification of more than one DNA segment can be achieved with Multiplex polymerase chain reaction (PCR) using primers tagged with unrelated nucleotide sequences which are then ligated together into a single DNA molecule (Chamberlain et al. (1988) Nucleic Acids Research 16(23):11141-56). But PCR products amplified with primers lacking the unrelated nucleotide sequence are not reliably produced due to differences in hybridization kinetics among the primers, and it is therefore necessary to tag each primer with an identical nucleotide sequence to achieve efficient amplification of multiple sequences. All of the PCR products then contain identical unrelated sequences which have to be removed or extended before they are linked to form one DNA molecule containing all sequences of interest.

One method of amplifying several DNA segments which occur in non-adjacent portions of a DNA sample, termed "splicing by overlap extension" (U.S. Pat. No. 5,023,171), assembles DNA molecules at precise junctions without the use of restriction enzymes or ligase. Component fragments to be recombined are generated in separate polymerase chain reactions using uniquely designed primers which produce amplicons having complementary termini to one another. Upon mixing and denaturation of these amplicons, strands having complementary sequences at their 3' ends overlap and act as primers for each other. Extension of this overlap by DNA polymerase produces a nucleic acid molecule in which the original sequences are spliced together. Subsequent rounds of PCR amplify the resulting spliced polynucleotide. This technique requires time to optimize primer sequences and amplification conditions to produce desired products. Each junction between the fragments to be spliced together must be individually considered, and a pair of primers must be designed for each target DNA fragment in order to make the ends compatible. Considerations for the design of PCR primers, (e.g., melting temperature, G-C content, avoidance of hairpin and dimer formation, and stringency for false priming sites) become increasingly complex as the number of fragments to be spliced in the reaction increases, such that combining more than just three or four target DNA segments becomes an insurmountable PCR reaction design problem. In addition, splicing by overlap extension performs the linker tagging and amplification in each site in a separate reaction, and subsequent reactions are used to assemble the pieces. This limits the usefulness of this technique from a genotyping approach although it is an effective gene construction technique.

The present inventors have previously demonstrated novel methods that provide for the rapid and ordered assembly of non-adjacent polynucleotides from a heterogeneous DNA population ("TRACE" technology; PCT Pub. No. WO 2015/120403). Particularly, those methods facilitate the assembly of a number of polynucleotides with minimal manipulation and characterization of intermediate products into a single DNA molecule in suitable quantity for accurate characterization of mutations within the assembled DNA fragments and with efficient, high-throughput processing that enables the characterization of multiple mutations that interact to create a specific phenotype.

However, many multiplexed editing technologies operate on 20-30 sites, and may require identification of subtle fitness changes outside the sensitivity of the inventors' previous methodologies. In addition, the results of the previous technologies are often surrounded by crossover noise which reduces the effectiveness of identifying rare mutants. Therefore, a new approach is desired which builds on the principles developed in the inventors' previous technology to identify an unlimited number of sites with less crossover noise, while enabling highly sensitive quantitative tracking. These and other needs can be met by the methods of the present invention.

SUMMARY

The present inventors have now developed a new approach to identify an unlimited number of sites with less crossover noise than the inventors' previous techniques ("TRACE" technique, described in detail in PCT Patent Application No. PCT/US15/15058 (WO 2015/120403); and Zeitoun, R. et al. Multiplexed tracking of combinatorial genomic mutations in engineered cell populations, *Nat. Biotechnol.* 2015, 33(6):631-7; which are incorporated herein by reference, in their entirety). The new approach of this disclosure enables highly sensitive, quantitative tracking.

In genetic engineering, combinations of mutations contribute to the phenotype of a cell. Although, as noted above, methods exist to create combinations of mutations in populations of cells, tracking this combinatorial mutation space is time consuming and costly. The inventors' previously-developed TRACE technique allows the tracking of combinations of mutations in a population by assembling all targeted mutations in a single construct compatible with high-throughput sequencing technologies. That technique was effective at identifying small mutations (<10 nt) occurring at 6-10 sites. It was also used to identify fitness changes by measuring the population dynamics with respect to selective pressures. But multiplexed editing technologies often operate on 20-30 sites, and may require identification of subtle fitness changes far outside the sensitivity of TRACE. Additionally, TRACE results are often surrounded by crossover noise which reduces the effectiveness of identifying rare mutants. Therefore, the inventors have developed the new methodology of this disclosure, which builds on the principles developed in the TRACE technology, to identify an unlimited number of sites with less crossover noise than TRACE. This new approach also enables highly sensitive quantitative tracking.

Thus, the methods of this disclosure can be used to track combinations of mutations in populations by coupling DNA assembly and paired-end sequencing technology with high-throughput sequencing. This approach works by using the transformation of a population of cells (for example, *E. coli*) with a unique barcode contained on a high-copy plasmid. Each cell in the population has a unique barcode which can then be used to identify the genotype of the cell. For qualification (to identify the genotype of cells in a population) barcodes are assembled in emulsion with sites of interest using multiplexed PCR. For example, if 20 sites are genotyped, then 20 barcode-sites are assembled per cell. These binary assemblies can then be sequenced using paired end sequencing technology (such as the Illumina MISEQ™) to reveal which barcodes correspond to which genotypes. This approach allows for an unlimited number of sites to be identified. Additionally, this methodology allows sites to be sequenced across several replicates as barcode-genotype correlations are static. To measure fitness data, barcodes can simply be sequenced with high-throughput short sequencing read technology (such as the Illumina HISEQ™). Therefore, selections can be rapidly performed on populations of known combinatorial genotypes.

Similar to the inventors' previous, technology (TRACE), the methodology of this disclosure uses the coupling multiplexed DNA assembly for genotype identification. TRACE performs quantification and qualification in a single sequencing run, and all sites are assembled into one construct, but that limits the length and number of sites that can be identified in a single run. Additionally, quantification from assembly frequencies is an inefficient way of measuring cell compositions because assembling and amplifying DNA introduces quantitative noise. In contrast, in the binary assembly methods of this disclosure, quantification and qualification are decoupled, enabling a higher resolution view of both the population genotype frequency and composition. Additionally, binary assemblies of barcoded sites are easier to assemble than the multiplexed TRACE assemblies and may therefore be generated with less crossover in less time. Finally, quantification does not require an emulsion PCR step as barcodes are directly amplified.

This Summary of the Invention is neither intended nor should it be construed as being representative of the full extent and scope of the present invention. Moreover, references made herein to "the methods of this disclosure" or aspects thereof, should be understood to mean certain embodiments of the present invention and should not necessarily be construed as limiting all embodiments to a particular description. The present invention is set forth in various levels of detail in the Summary of the Invention as well as in the attached drawings and the Description of Embodiments and no limitation as to the scope of the present invention is intended by either the inclusion or non-inclusion of elements, components, etc. in this Summary. Additional aspects of the present invention will become more readily apparent from the Description of Embodiments, particularly when taken together with the drawings.

BRIEF DESCRIPTION OF DRAWINGS

FIG. 1*a* is a schematic depicting transformation of a combinatorial engineered population with a random barcode on a high copy-number plasmid. FIG. 1*b* depicts direct sequencing of barcodes to quantify the frequency of barcodes in a population.

DESCRIPTION OF EMBODIMENTS

The present disclosure is drawn to high-throughput methods for tracking mutations across potentially dozens of sites simultaneously with high quantitative accuracy.

In the methods of this disclosure, plasmid encoded unique nucleic acid sequences ("barcode" sequences) provide a cell-specific unique identifier. These plasmid-based unique identifiers are short enough to be quantitatively tracked by the highest throughput sequencing approaches. Each cell-specific barcode is linked to a specific combinatorial genotype via a multiplexed binary assembly reaction, performed in emulsion. Binary assemblies are then sequenced in multiplex via paired-end high-throughput sequencing. As such, the linkage of the same barcode with multiple targeted sites indicates that the nucleic acid sequences located in those sites are from the same cell. Thus, this linkage map contains specific sequence information on each of the targeted nucleic acid sites, with the remainder of the genome unaltered and a single barcode. Primers and linkers used in these methods are designed to be orthogonal to prevent primer-dimers while assembling into multiple binary complexes. Use of a high-copy plasmid may avoid potential assembly bottlenecks when attempting to link a plurality of sites in a genome with a single plasmid based barcode (as predicted by mathematical modeling). In these methods, the effect of copy number variation on barcode quantification variation is predicted to be <1% for a genotype occurring at a frequency of at least $10^{-5}$ (in a 1 mL OD600=1 population, or approximately $10^9$ cells).

Figure 9:
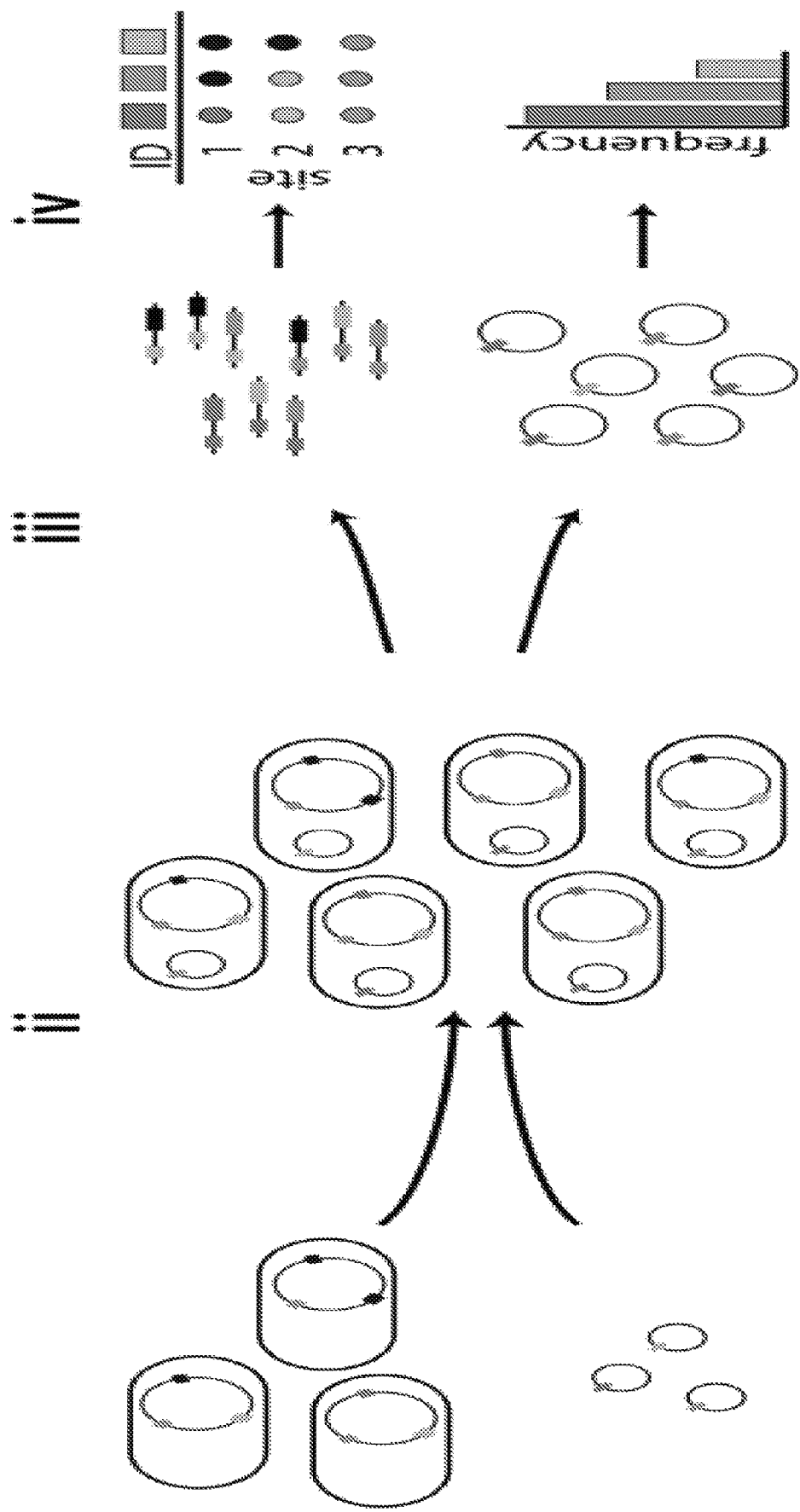
FIG. 9 is a schematic depicting a summary of this methodology for tracking of mutations across several dozen sites simultaneously.

FIG. 9 depicts one embodiment of the mutation tracking methods of this disclosure for illustrative purposes.

An exemplary embodiment of the methods of this disclosure include a method to track combinations of mutations in populations, including transforming a population of cells with a plasmid comprising a heterologous nucleic acid sequence to form a population of cells comprising a unique nucleic acid barcode sequence. The genetic sites of interest are assembled with unique nucleic acid barcode sequences by multiplexed polymerase chain reaction (PCR) to form a binary assembly of genetic sites of interest linked to each unique nucleic acid barcode sequence. Each binary assembly is sequenced by paired end sequencing to determine which nucleic acid barcode sequences correspond to each genetic site of interest.

Linker sequences may be included in the assembly reaction to provide the separate component polynucleotides with complementary termini that are utilized in a splice overlap extension assembly reaction.

The PCR assembly conditions used are typically 35 cycles. The addition of 100 μM nucleotide triphosphates are added per site linked per reaction. The reaction occurs with an anneal temperature of 60° C. The annealing time used is 30-60 seconds. The PCR amplification conditions can be any PCR amplification conditions deemed suitable by those of skill in the art, including those described in PCR Technology: Principles and Applications for DNA Amplification, ed. H A Erlich, Stockton Press, New York, N.Y. (1989); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17; and U.S. Pat. Nos. 4,683,202 and 4,965,188, each of which are incorporated herein by reference. In certain embodiments, the PCR step of the amplification reaction comprises 15 to 30 cycles of denaturation, annealing, and extension in the presence of primers complementary to primer binding segments. In certain embodiments, the annealing and extension steps of the PCR can both be performed at 60° C. and 72° C., respectively. However, one of skill in the art will understand that optimal conditions for successful amplification will depend on the thermostable DNA polymerase and the linker sequences utilized, and these conditions may be adjusted accordingly. Emulsion PCR techniques are described in Griffith, Tawfick Trends in Biotechnology 2007 and Wetmur, et al. (2005) Nucleic Acids Research 33(8):2615-2619.

Optionally, the assembled polynucleotide can be purified by any technique known to one of skill in the art (e.g., gel electrophoresis purification methods) and used for a variety of purposes, such as analysis of the assembled DNA sites. This analysis may include any well-known DNA analysis, including, for example, RFLP analysis or DNA sequencing. In preferred embodiments, the assembled polynucleotide sites are sequenced using next generation sequencing technologies (such as Illumina's MiSeq™).

The thermostable DNA polymerase used in the assembly reactions to produce the single assembled polynucleotide and in the amplification reactions to amplify the single assembled polynucleotide, may be any thermostable DNA polymerase deemed suitable by those of skill in the art. Thermostable DNA polymerases suitable for use in the present methods include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu or DEEPVENT™) DNA polymerase, *Pyrococcus woosii* (Pwo) DNA polymerase, *Bacillus sterothermophilus* (Bst) DNA polymerase, *Sulfolobus acidocaldarius* (SAC) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, and mutants, variants, and derivatives thereof. Thermostable DNA polymerases having high fidelity (i.e., proofreading properties) and low error rates are preferred.

Another aspect of the invention is the application of the methods of this disclosure to mammalian cells in which the unique nucleic acid barcode sequences may be introduced into the mammalian cells by either infecting individual cells with a barcoded virus, or by using a hyper-variable region within the mitochondria of the mammalian cell. In the second scenario, the multi-copy mitochondrial site is analogous to the barcoded plasmid used in bacteria and the hypervariable region is analogous to the barcode on the high copy number plasmid. Hence, the barcode is cell line specific (as opposed to cell specific). This approach may be useful in rapidly assessing a large number of mutational hotspots for choosing the ideal targeted therapy for cancer patients, both in cases of finding the suitable drug to treat a tumor harboring a single mutation (Paez, et al., 2004 "EGFR Mutations in Lung Cancer: Correlation with Clinical Response to Gefitinib Therapy." Science 304 (5676): 1497-1500; Yarden, et al., 2012 "The ERBB Network: At Last, Cancer Therapy Meets Systems Biology." Nature Reviews. Cancer 12 (8): 553-63) and in more complex situations in which there are more than a single oncogenic mutation and their combined effect should be taken into account (Lièvre, et al., 2006 "KRAS Mutation Status Is Predictive of Response to Cetuximab Therapy in Colorectal Cancer." Cancer Research 66 (8). AACR: 3992-95).

An automated software tool, useful for the design of primers and linkers used in the methods of this disclosure was developed, and is described in detail in PCT/US2015/015058, (Publication No. WO/2015/120403, 13 Aug. 2015; incorporated herein by reference).

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1

Library Preparation

Libraries are prepared using the multiplexed genome engineering technique (MAGE) in the HME63 strain. Oligomers (90-mer) are generated using the MODEST tool and degeneracy is designed with the ribosome binding site calculator. After 12 rounds of MAGE (with an equimolar oligomer concentration) the population is transformed with barcoded plasmids generated using circular polymerase extension cloning (OPEC) between a de novo synthesized barcode ($N_{15}$) and the pUC57-kanR plasmid. The library is transformed with a varying concentration of plasmid. These cells are plated and measured to ensure only one plasmid is transformed per cell. Cells are grown in carbinacillen and kanamycin to ensure the population selected for contains a plasmid. Finally, cells are diluted to around $10^3$-$10^4$ cells (measured by dilution plating) to ensure the population is focused enough for accurate assessment and non-repeating barcodes.

Assembly Primer Design

To perform barcode-site assembly, a custom MATLAB program was used which designs primers and linkers. This tool is modified from the original TRACE tool. One set of homology sequences are used to amplify the barcode, and N sets of primers are used to amplify N sites. Barcodes are generated using CPEC between random ($N_{15}$) DNA sequences and a pUC57 backbone. We estimate around $10^6$ unique barcodes are generated and amplifying barcodes results in DNA bands of the correct size. To assemble these sites, a randomly generated linker (passing thermodynamic constraints) is designed and attached to the reverse barcode primer and forward site primer. More than one linker sequence is needed to ensure linkers are compatible with covalent attachment to forward site primers, but only one linker is used per site. Finally, each reverse site has a linker sequence attached to ensure strong amplification of assemblies during sequencing preparation.

Assembly and Sequencing

Figure 1C:
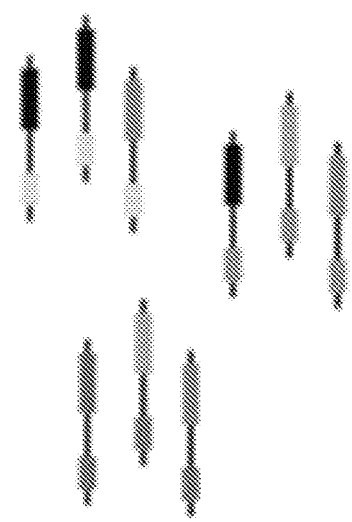
FIG. 1*c* depicts the assembly of barcodes and engineered sites into a binary assembly using multiplexed emulsion PCR-based assembly to qualify the genotypes in a population.
Figure 1C:
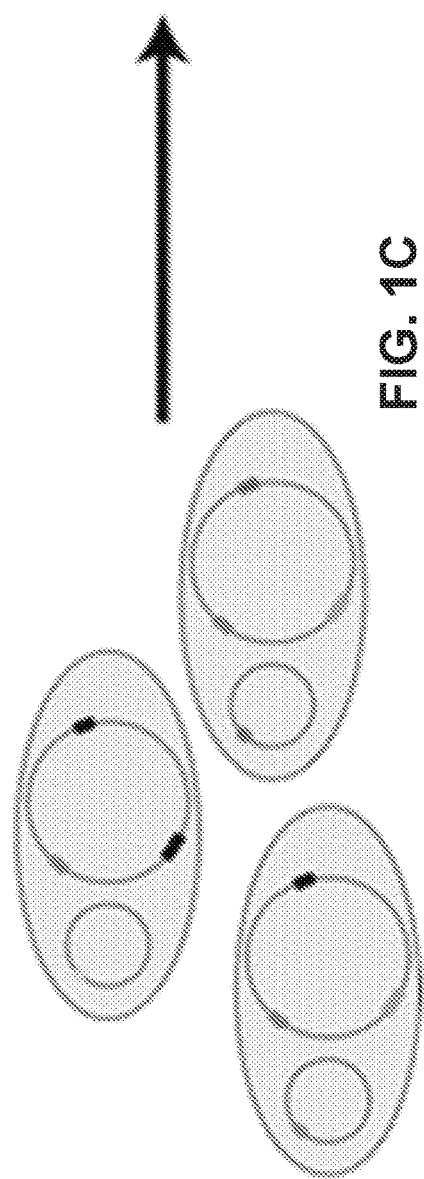
Figure 10:
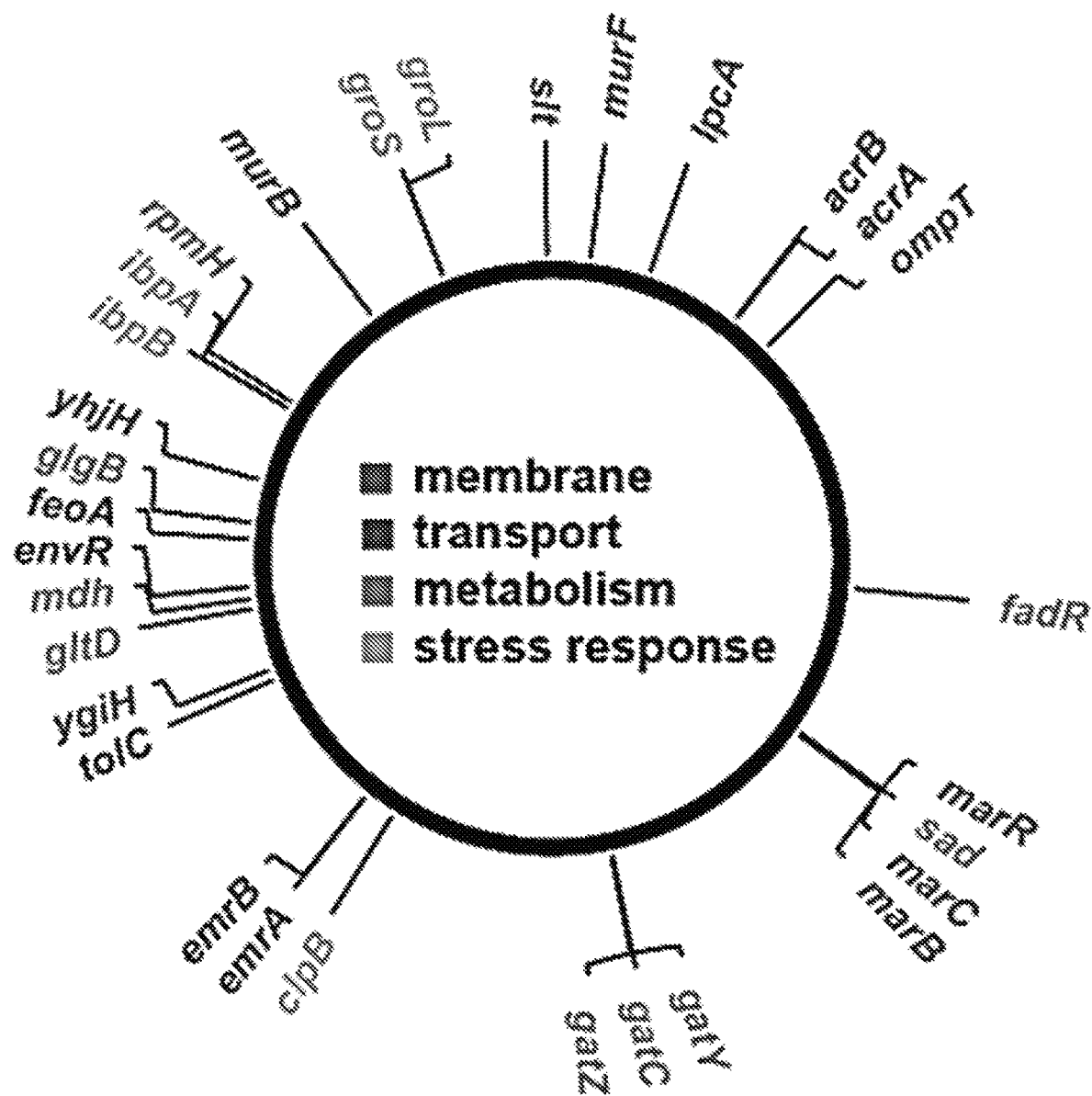
FIG. 10 is a map depicting the location and identification of targeted genes on a combinatorially-engineered library targeting the ribosomal binding site (RBS) of 31 genes expected to enhance growth in the presence of alcohols.

Assembly is performed in emulsion as previously performed in the TRACE technique (described in detail in PCT Patent Application No. PCT/US15/15058). Cells are loaded at OD 0.1 to ensure most vessels contain one cell. DNA is extracted using isobutanol, heat and centrifugation, and then gel purified. Subsequently, DNA is amplified with pre-adapter and adapter primers to enable coupling of assembled sequences on the sequencer. FIGS. 1A-1C show a general overview of techniques of this disclosure. As depicted in FIG. 1A, a combinatorial engineered population is transformed with a random barcode on a high copy-number plasmid. The population is then diluted to a desired number of unique genotypes ($10^3$-$10^4$). As depicted in FIG. 1B, to quantify the frequency of barcodes in a population, barcodes can be directly sequenced (e.g., using the Illumina HISEQ™ sequencing system). As depicted in FIG. 10, to qualify the genotypes in a population, barcodes and engineered sites are assembled into a binary assembly using multiplexed emulsion PCR-based assembly. These binary assemblies are then sequenced (e.g., using paired end Illumina MISEQ sequencing).

Figure 2:
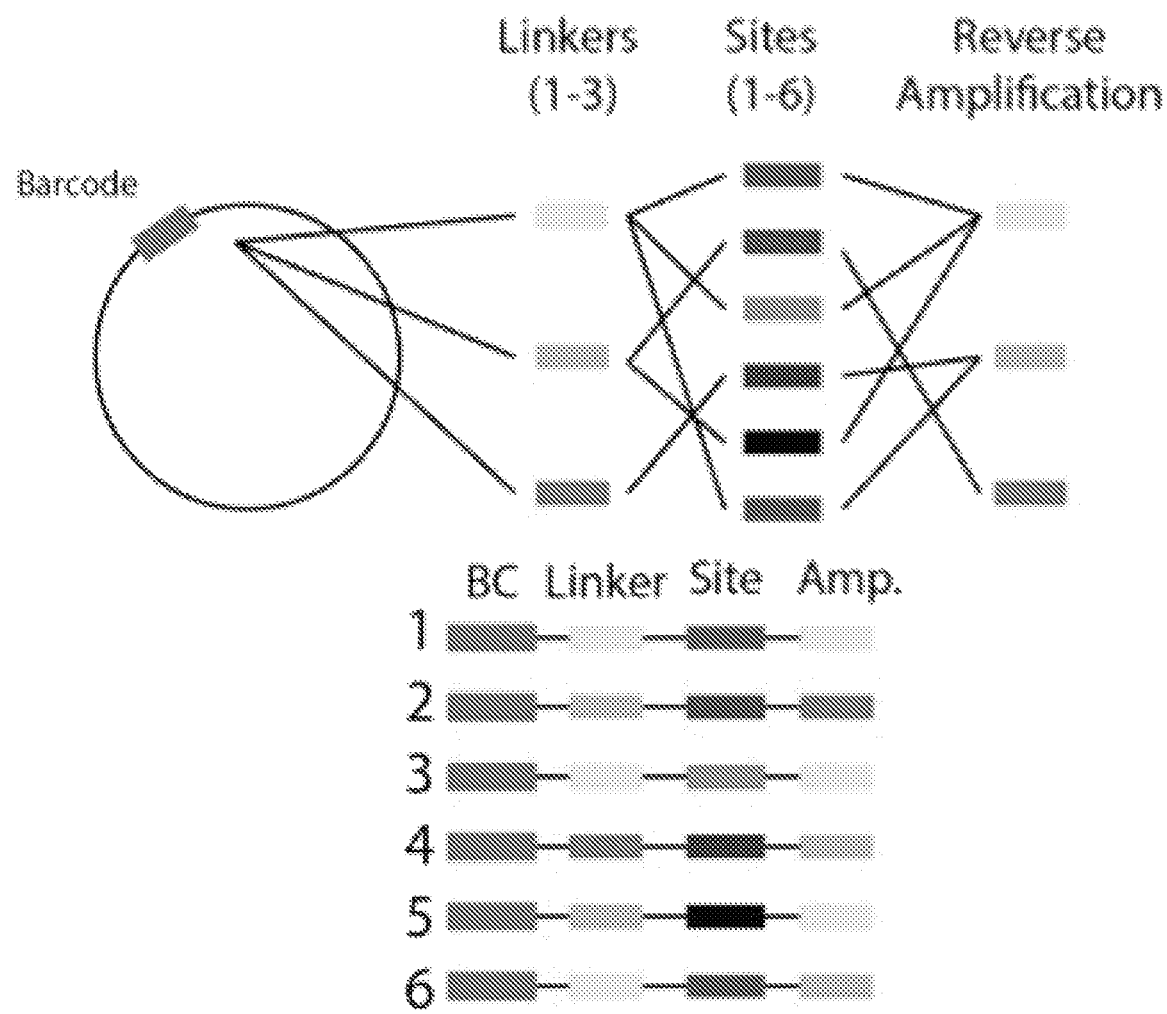
FIG. 2 depicts a construct and assembly design for assembling six sites, with three linkers, and three universal reverse sites according to methods of this disclosure.

FIG. 2 depicts the general construct and assembly design for assembling six sites, with three linkers, and three universal reverse sites. To perform the depicted multiplexed assembly, barcodes are linked to sites using a linker sequence. To make sure linker sequences are compatible with site amplification primers, many linker sequences is needed. In addition, a reverse amplification sequence is randomly generated and computationally tested to ensure multiplexed amplification of the correct band. (Primers were designed using an automated primer design tool.) The six assembled sites (FIG. 2, bottom) may then be amplified using a universal forward barcode primer, and three multiplexed reverse primers.

Figure 3:
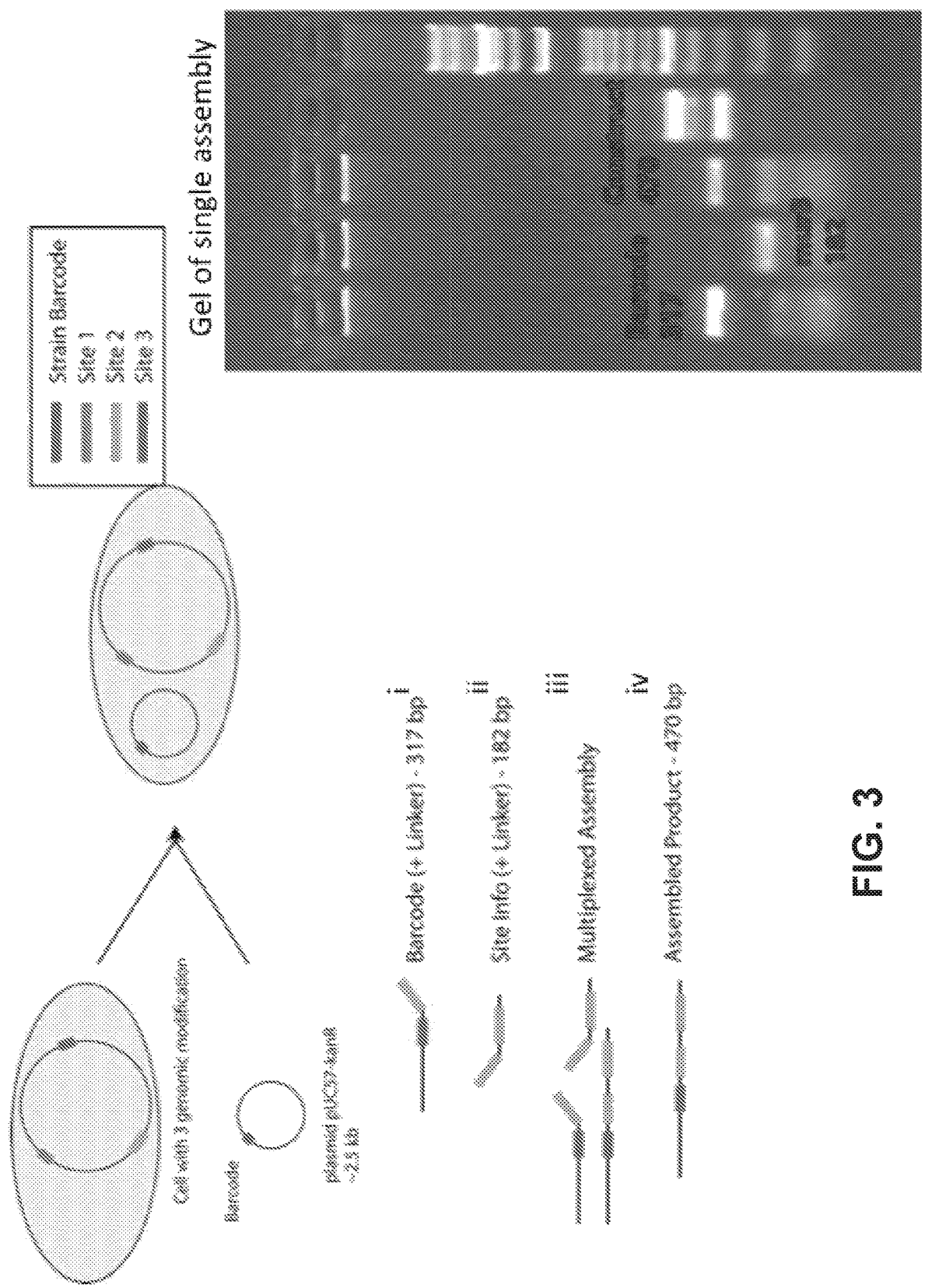
FIG. 3 shows the results of the assembly methodology depicted in FIG. 2.

FIG. 3 depicts the results of the assembly. Reference i) shows a barcode individually amplified with a linker sequence. Reference ii) shows a site (gene murB) individually amplified with a linker sequence. Reference iii) depicts the effects of performing these site and barcode amplifications together, resulting in both sequences amplified along with a larger tail (around 500 bp). Reference iv) depicts the assembled barcode-site amplified from iii) using a universal forward and reverse sequence. These constructs were analyzed by gel electrophoresis (FIG. 3, right, ladder is 100 bp ladder).

Figure 4:
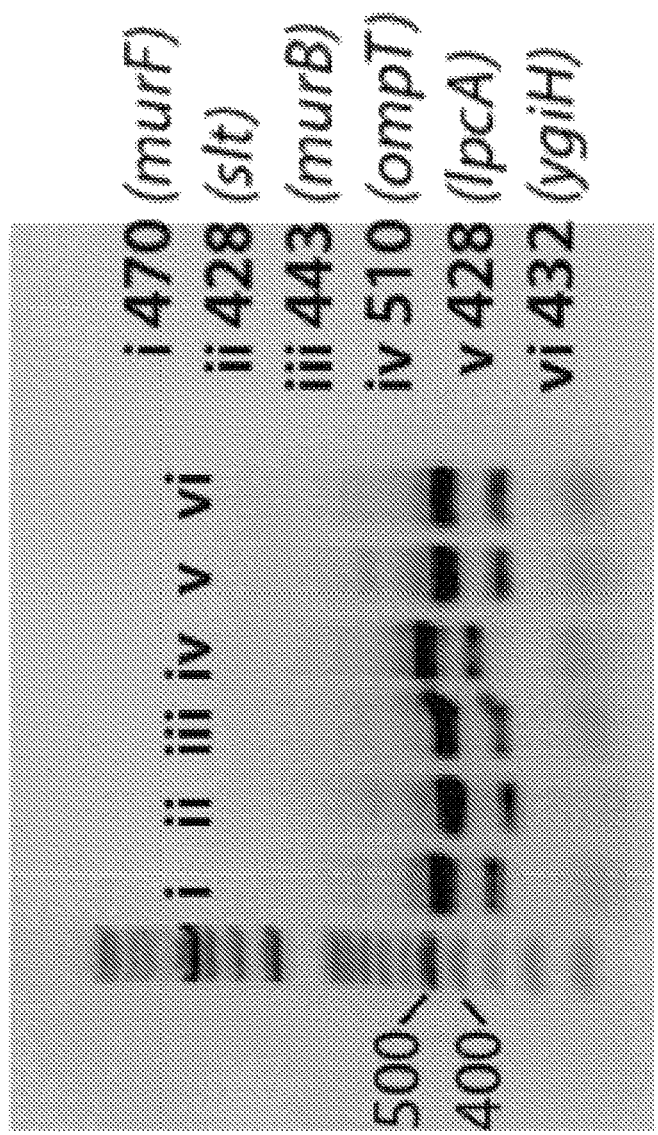
FIG. 4 depicts the assembly of six sites simultaneously to barcodes, in a single reaction according to methods of this disclosure.

FIG. 4 depicts the assembly of six sites performed simultaneously. In this case, six sites were assembled to barcodes in a single reaction. The assembly (FIG. 4, left, box) was gel extracted and each band of the correct barcode-site size was amplified from the assembled mixture with different primers, and analyzed by gel electrophoresis (FIG. 4, right). Sequencing of the bands confirmed that the sequence and barcode from different sites and two colonies match accordingly: the barcodes match within an organism, and the gene (individual site) sequences match between organisms.

To test this multiplexed assembly in a high throughput sequencing format, the genotype of a population was tested before and after three days of growth. Barcodes and site sequences matched in both cases.

Figure 5:
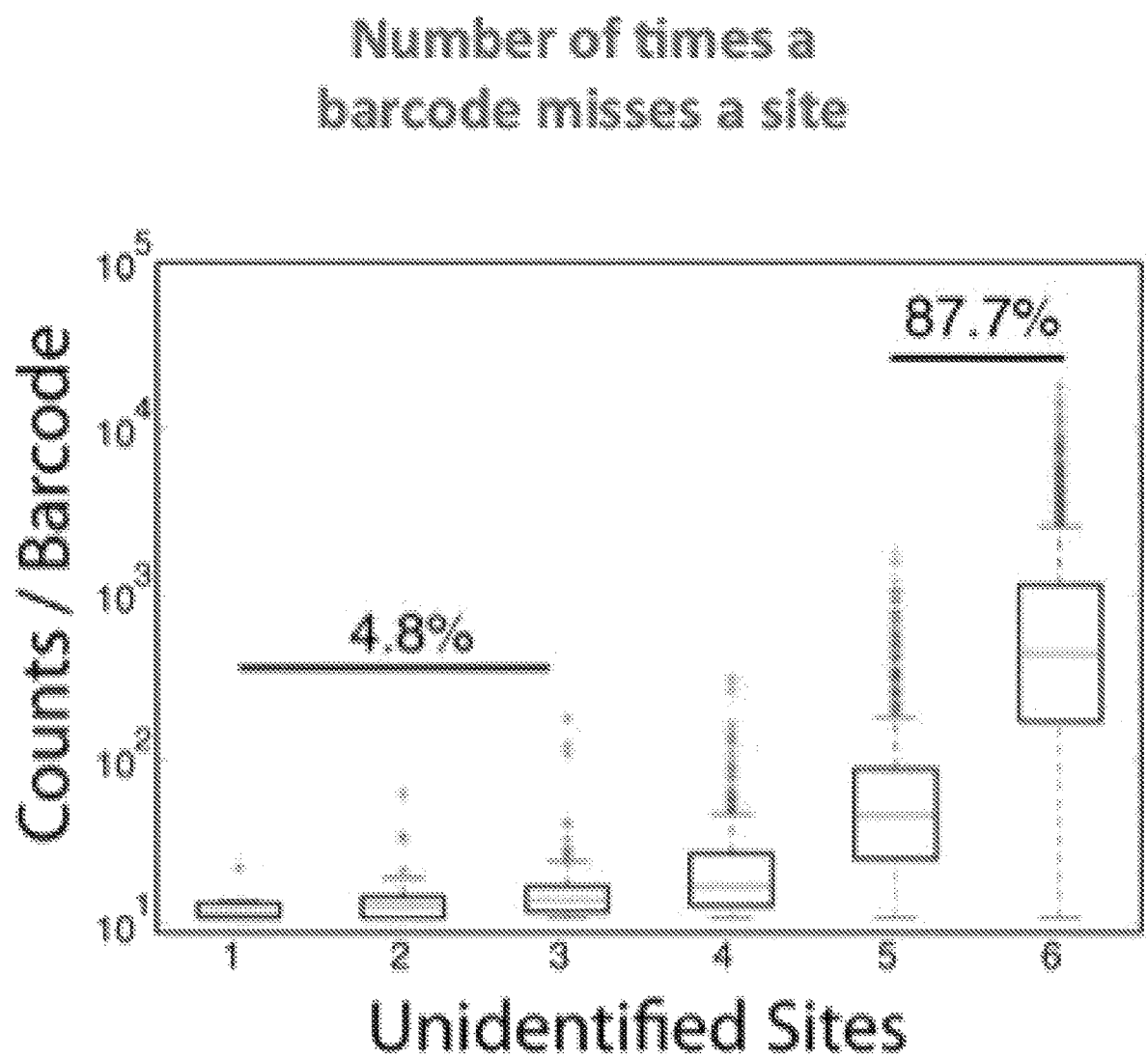
FIG. 5 shows the results of an assessment, via emulsion PCR assembly and high-throughput sequencing, of the assembly depicted in FIG. 4.
Figure 6:
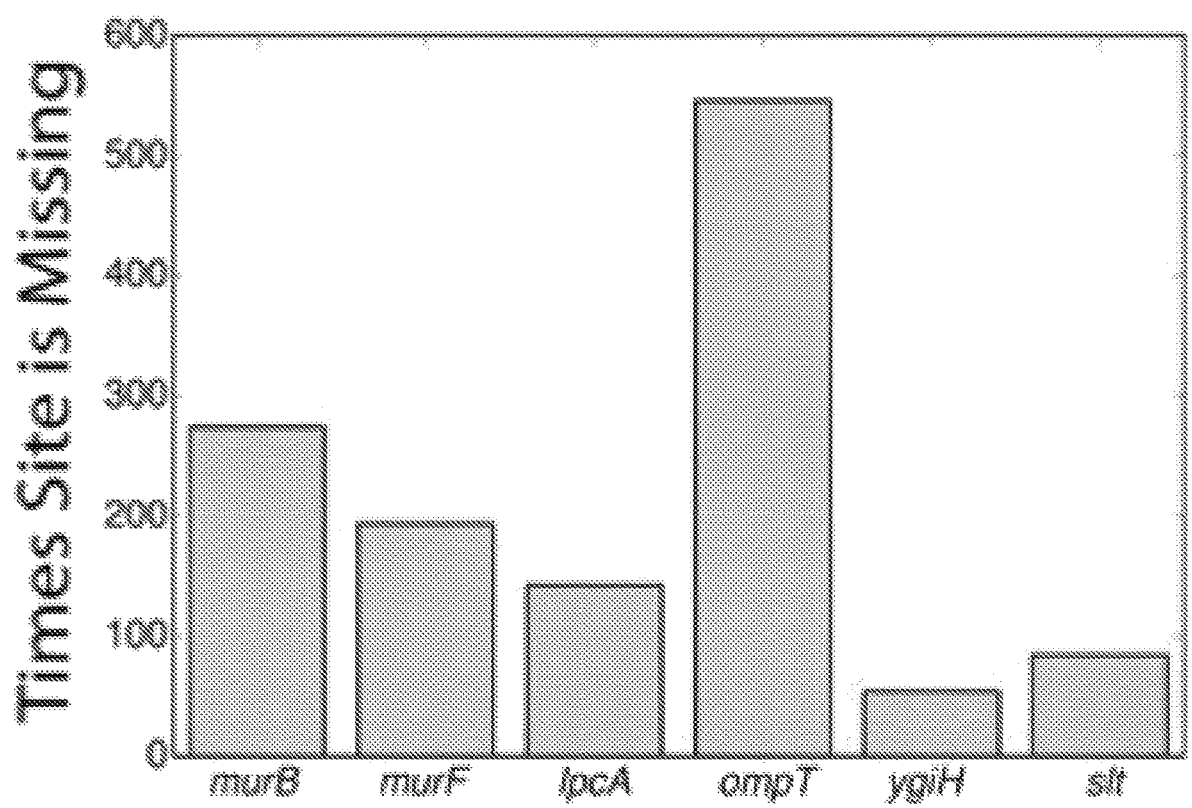
FIG. 6 shows a frequency of unidentified sites per barcode in the assessment of the assembly depicted in FIG. 4.

This proof of concept library was then assessed via emulsion PCR assembly and high-throughput sequencing. To ensure high sequencing coverage of the population (limited by sequencing throughput) the population was diluted to a few thousand cells from presumably over $10^6$ genotypes. Our sequencing data contained reads that link unique plasmid barcodes with each of the six targeted sites (barcode-site reads), the combination of which for a single barcode defines a unique, barcoded genotype. This process requires that there is enough redundancy in the binary assembly process that the same plasmid barcode is linked to each of the six different sites in the targeted genome. Here, 89% of the barcodes were linked with five or more sites (FIG. 5) and only about 5% were linked with three or fewer sites. These results also show that as the number of times a specific barcode shows up in the sequencing data, the more likely it is to be linked with larger number of targeted sites, suggesting that deeper sequencing would produce an even greater percentage of barcodes linked with all six targeted sites. The ompT and murB sites appear to be missing more than other sites (FIG. 6). This is presumably due to inefficiencies in assembly, site amplification and clustering. To address this, in a separate reaction the RBS of the ompT gene can be linked with the plasmid barcodes and sequenced deeply to develop the linkage map.

Figure 7:
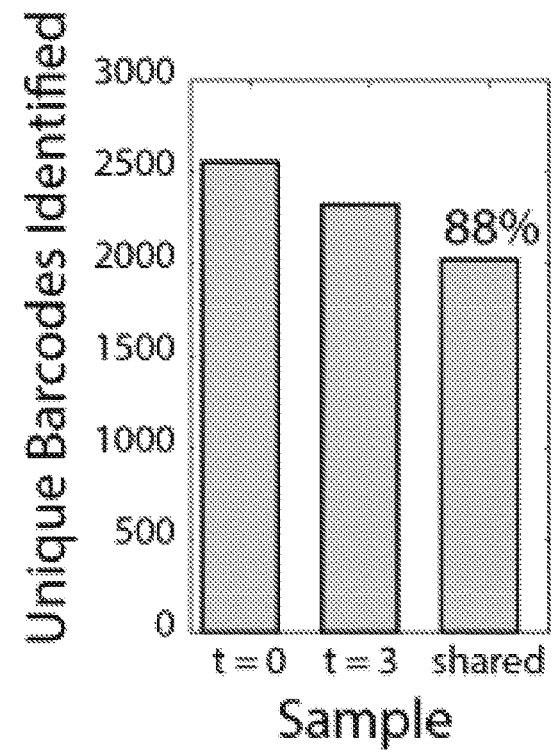
FIG. 7 shows the results of tracking the same combinatorial library before and after growth for three days, indicating that the barcode can act as a cell-specific unique identifier during growth selections.
Figure 8:
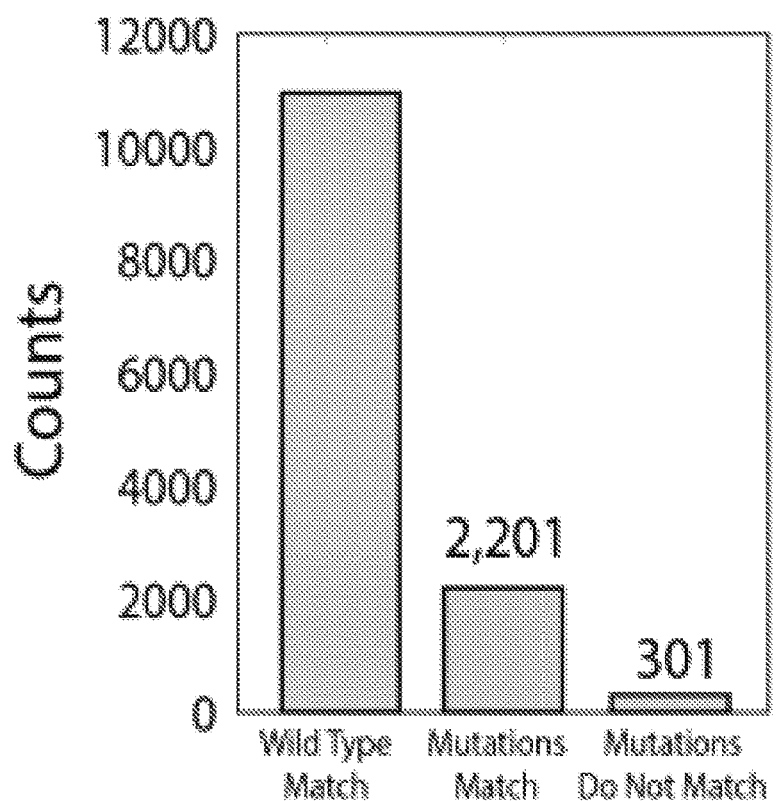
FIG. 8 shows frequency of mutations found in sequenced sites, identified at both time points.

This methodology was further validated by tracking the same combinatorial library before and after growth in minimal media for three days. Approximately 88% of the unique bTRACE genotypes (about 2,100) were present in both the original (t=0) population and selected (t=3) population (FIG. 7), indicating that the barcode can act as a cell-specific unique identifier during growth selections. We also examined the sequences of each of the six mutated sites at both time points (about 12,500 sequences). Approximately 20% of the sequenced sites contained mutations, 88% of which were identified at both time points thus demonstrating that this methodology is capable of tracking mutations with the same barcodes throughout growth selections (FIG. 8). This result also demonstrates that genotyping errors can be identified between replicates.

A schematic of the barcode transformation, and subsequent library quantification and qualification, summarizing this new methodology for tracking of mutations across several dozen sites simultaneously with high quantitative accuracy (referred to herein as "barcoded-TRACE" or "bTRACE"), utilizing plasmid-encoded barcode sequences to provide a cell-specific unique identifier is shown in FIG. 9. In step i) of these methods, a library is transformed with a barcode library. In step ii) of these methods, the population may be diluted to ensure high coverage of mutants. In step iii) of these methods, multiplex binary assemblies (or "barcodes") are extracted from the library, and in step iv), the population of binary assemblies is sequenced to link specific genotypes with specific barcodes and, separately, the population of plasmid-barcodes are sequenced to determine the distribution of the genotypes throughout the library population. The plasmid-based unique identifiers are short enough to be quantitatively tracked by the highest throughput sequencing approaches (e.g. HISEQ™). As depicted in FIG. 9, in a separate reaction, each cell specific barcode is linked to a specific combinatorial genotype via a multiplexed binary assembly reaction performed in emulsion. Binary assemblies are then sequenced in multiplex via paired-end high-throughput sequencing (e.g. MISEQ™). As such, the linkage of the same barcode with multiple targeted sites indicates that the sequences located in those sites are from the same cell. We define this linkage map throughout as a "bTRACE genotype" because it contains specific sequence information on each of the targeted sites linked to a single barcode, with the remainder of the genome unaltered. Primers and linkers are designed to be orthogonal to prevent primer-dimers while assembling into multiple binary complexes following many of the same principles developed in the TRACE method (the bTRACE software is freely available online for download).

Example 2

Figure 11:
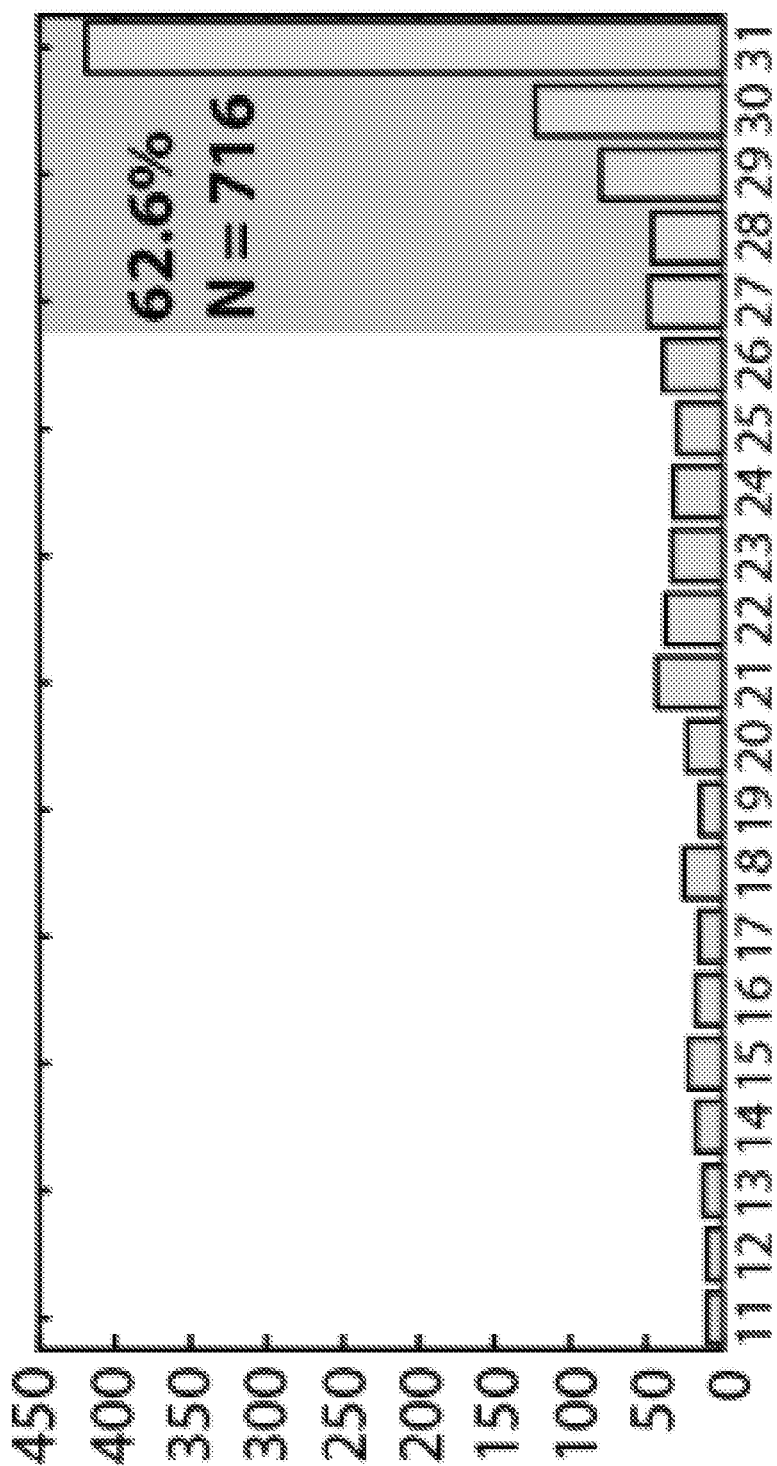
FIG. 11 shows the number of bTRACE genotypes containing sequencing data on the targeted sites.
Figure 12:
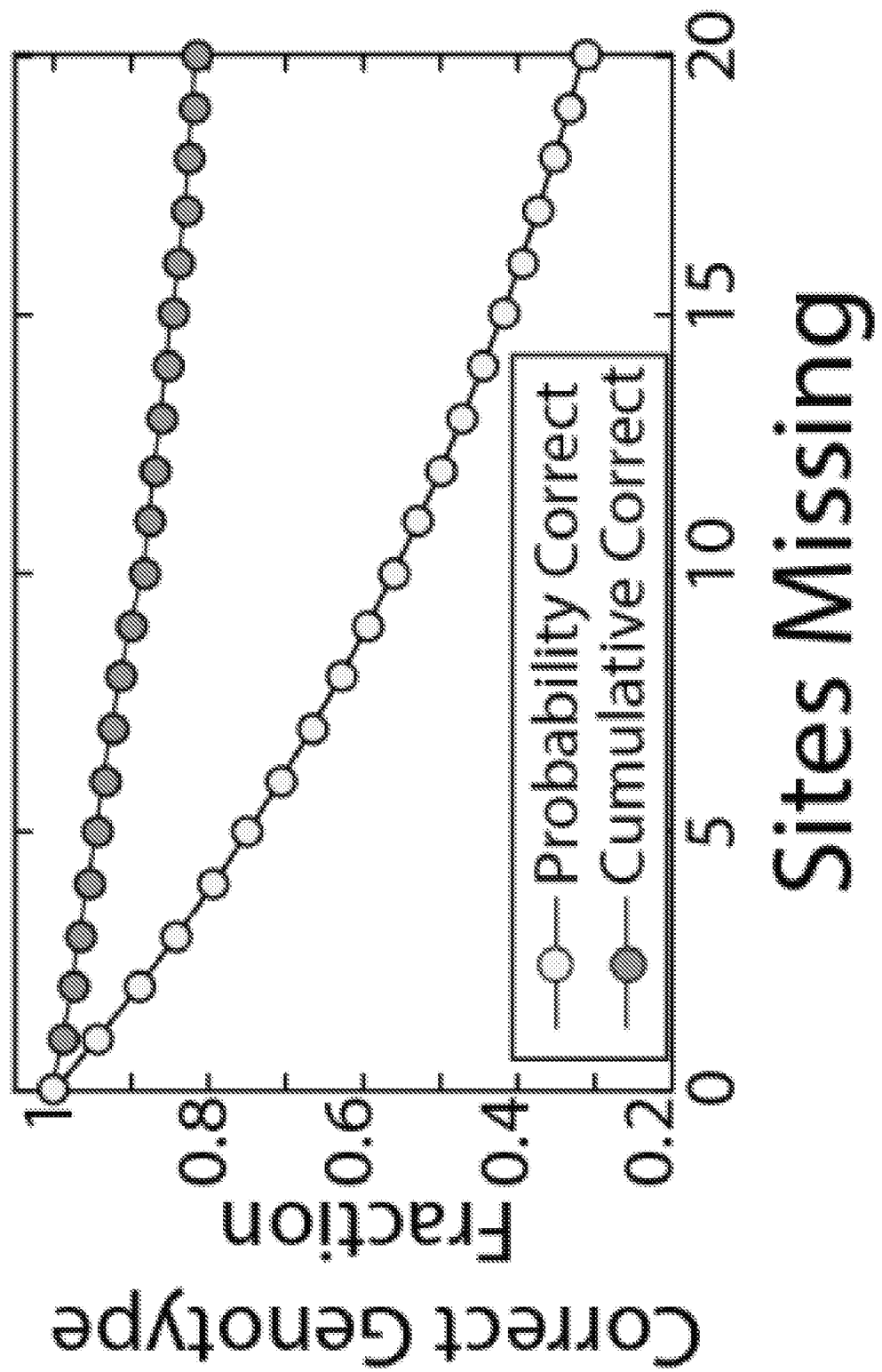
FIG. 12 shows the probability of identifying correct genotypes assuming unidentified sites are wild-type and the cumulative correct fraction of members with the population distribution of FIG. 11 data.
Figure 13:
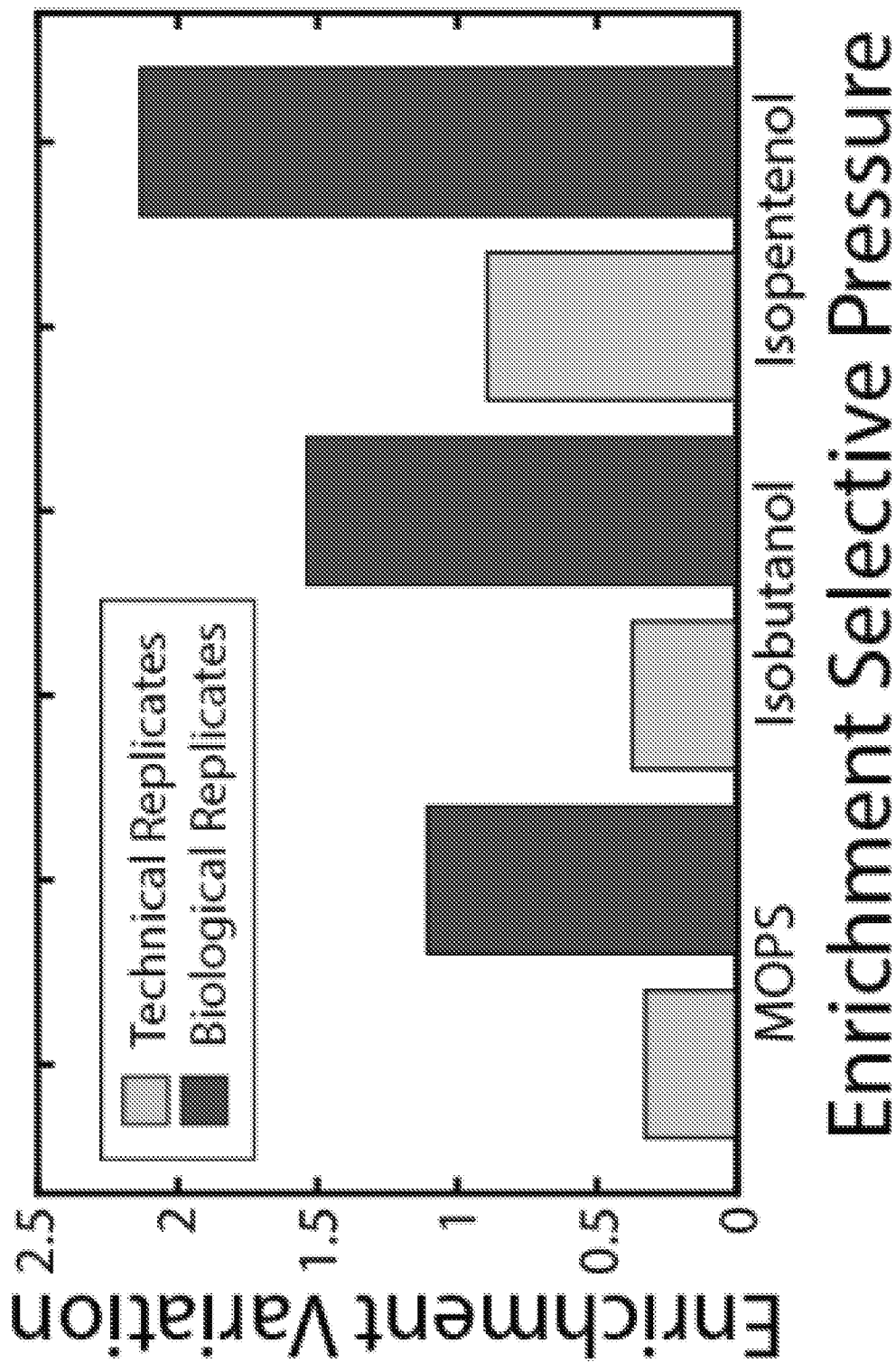
FIG. 13 shows a comparison of wild type genotype enrichment noise in the case of three selective pressures.

To assess the effect of targeted mutagenesis on isobutanol tolerance, the enrichment of genotypes was compared between minimal media and minimal media supplemented with isobutanol. This application of bTRACE was used to track a combinatorially-engineered library targeting the ribosomal binding site (RBS) of 31 genes expected to enhance growth in the presence of alcohols. FIG. 10 depicts the location and identification of targeted genes on E. coli's genome. In this case, a bTRACE genotype is determined by performing multiplex binary assembly of the RBS for all of the targeted sites with a unique barcode. Tracking of the library population is performed by monitoring the barcode distribution at different time-points. FIG. 11 shows bTRACE genotype coverage. 62.6% of bTRACE genotypes contained sequencing data on 27 or more of the targeted sites. FIG. 12 shows the probability of identifying correct genotypes, assuming unidentified sites are wild-type and the cumulative correct fraction of members with the population distribution of FIG. 11 data. FIG. 13 shows a comparison of wild type genotype enrichment noise in the case of three selective pressures. A comparison of differential enrichment scores from MOPS media and MOPS media supplemented with isobutanol, for identical genotypes identified different genotyped barcodes having 27 or more reads, including data points found to differ between enrichments (p<0.05). This data produced a histogram of differentially-enriched bTRACE genotypes based on the number of mutated sites identified out of the 31 targeted sites.

It was observed that an isobutanol susceptible sub-population emerged when challenging libraries with strong selective pressures, which accounts for the greatly increased biological variation. This sub-population is centered with a MOPS enrichment of −1 and isobutanol enrichment of −3. This can be clearly observed when visualizing the histogram of differential enrichment, where differential enrichment is defined as the difference between the enrichment in isobutanol and enrichment in MOPS. The lack of a clear distinction of differential enrichment between mutant genotypes and wild type genotypes was clear and emphasized the significance of biological replicates.

These examples validate the methods of this disclosure, which quantitatively track and identify combinations of mutations, with a proof of concept 6-site library and then expanded to track 31-sites in a population. With the ability to track larger numbers of targeted sites, interactions among mutations at the biological sub-system scale (metabolic pathways, regulatory networks, protein complexes) can now be measured and used to inform more complex engineering efforts. Using this approach, we were able to identify the substantial role biological noise plays in assessing combinatorial engineered libraries. This is something that has not been previously identified in a broad sense and can help direct more informed genome engineering efforts. Another question that arises is how to deal with biological replicates with stochastically-generated genome engineered populations.

With the bTRACE methodology of this disclosure, once barcode-site correlations are developed in a library, numerous selections can be easily performed and measured. While our libraries only covered about 103 cells, next-generation high-throughput sequencing strategies will enable 100-fold deeper library interrogation, or interrogation of 100's of sites in parallel, thus allowing extension of these methods to enable the engineering of multiple sub-systems in parallel. Finally, this approach is expandable to many systems and approaches. For example, barcodes can be used on low copy number plasmids or may be genomically-integrated. Based on our experience, assembly should occur between multiple sites and a single barcode, although less efficiently than with a high-copy number plasmid. In addition, plasmids may be used with a wide-variety of species (including mammalian), and barcodes may be genomically integrated into many species, for example with the advent of CRISPR/Cas9 technologies.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method for tracking combinations of mutations in one or more genetic sites of interest in cell populations comprising:
    a. transforming a population of cells comprising a heterologous nucleic acid sequence to form a population of cells comprising a unique nucleic acid barcode sequence;
    b. assembling genetic sites of interest comprising genetic sites of interest having one or more mutation with the unique nucleic acid barcode sequences by multiplexed polymerase chain reaction (PCR) to form a binary assembly of genetic sites of interest comprising the genetic sites of interest having the one or more mutation linked to each unique nucleic acid barcode sequence; and
    c. sequencing each binary assembly by paired end sequencing to determine which unique nucleic acid barcode sequences correspond to each genetic site of interest.

2. The method of claim 1, wherein the heterologous nucleic acid sequence is about 15 nucleotides in length.

3. The method of claim 1, wherein the genetic sites of interest are discrete genes.

4. The method of claim 1, wherein the genetic sites of interest are comprise discrete genes having specific genetic mutations.

5. The method of claim 1, wherein the multiplexed PCR comprises PCR amplification in a reaction comprising a linker nucleic acid sequence to form the binary assembly of constructs having a constructed order comprising: a unique nucleic acid barcode sequence—linker—genetic site of interest comprising a genetic site of interest having one or more mutation—reverse amplification nucleic acid sequence.

6. The method of claim 1, wherein the transforming a population of cells comprises transforming the population of cells with a plasmid.

7. The method of claim 1, wherein the multiplexed PCR reaction comprises a DNA polymerase, selected from the group consisting of *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu or DEEPVENT™) DNA polymerase, *Pyrococcus woosii* (Pwo) DNA polymerase, *Bacillus sterothermophilus* (Bst) DNA polymerase, *Sulfolobus acidocaldarius* (SAC) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* DNA polymerase, ethanobacterium thermoautotrophicum (Mth) DNA polymerase, and mutants, variants, and derivatives thereof.

8. The method of claim 5, wherein the multiplexed PCR is conducted under conditions suitable for denaturing the nucleic acid molecules and annealing of a linker sequence linked to one unique nucleic acid barcode sequence with a complementary linker sequence linked to one genetic site of interest comprising a genetic site of interest having one or more mutation to form the assembled construct comprising: a unique nucleic acid barcode sequence—linker—genetic site of interest comprising a genetic site of interest having one or more mutation—reverse amplification nucleic acid sequence.

9. The method of claim 8, wherein the linker sequences are independently at least 24 nucleotides in length.

10. The method of claim 1, wherein the multiplexed PCR amplification step is conducted for 35 cycles.

11. The method of claim 1, further comprising:
    d. sequencing the unique nucleic acid barcode sequences on each binary assembly by high-throughput short sequencing read technology.

12. The method of claim 1, wherein the population of cells comprises mammalian cells and the unique nucleic acid barcode sequence is transformed into the mammalian cells on a barcoded virus.

13. The method of claim 1, wherein the population of cells comprises mammalian cells and transformation of the mammalian cells with the unique nucleic acid barcode sequence comprises using a hyper variable region within mitochondria in the mammalian cells.

14. The method of claim 6, wherein the plasmid comprises a high copy number plasmid.

15. The method of claim 1, wherein tracking mutations comprises tracking mutations across dozens of genetic sites of interest simultaneously.

16. The method of claim 1, wherein the population of cells comprises eukaryotic cells.

17. The method of claim 1, wherein the population of cells comprises prokaryotic cells.

18. The method of claim 1, wherein the population of cells comprises bacterial cells.

19. The method of claim 1, wherein the number of barcodes in a population of cells is equal to each novel genetic site of interest having the one or more mutation plus any wild type genetic site of interest not containing one or more mutation.

20. The method of claim 1, wherein the population of cells comprises mammalian tumor cells.

21. The method of claim 1, wherein the genetic site of interest having one or more mutation comprises one or more rare mutations in the genetic site of interest.

22. The method of claim 21, wherein the one or more rare mutations in the genetic site of interest comprises a rare combination of mutations in the genetic site of interest.

23. The method of claim 1, further comprising, (d) identifying all sequences of the genetic sites of interest found in a single cell of the population of cells.

* * * * *